United States Patent [19]

Felder et al.

[11] 4,278,808

[45] Jul. 14, 1981

[54] METHOD OF PREPARING A 3-ALKOXY-2-ALKYL-PROPIONIC ACID ESTER DERIVATIVE AND INTERMEDIATE THEREFOR

[75] Inventors: Ernst Felder, Riva S. Vitale, Switzerland; Davide Pitre, Mailand, Italy

[73] Assignee: Bracco Industria Chimica S.p.A., Milan, Italy

[21] Appl. No.: 942,403

[22] Filed: Sep. 14, 1978

[30] Foreign Application Priority Data

Oct. 31, 1977 [CH] Switzerland .................. 13188/77

[51] Int. Cl.³ .................. C07C 69/734; C07C 69/63; C07C 69/67
[52] U.S. Cl. .................. 560/183; 560/184; 560/186
[58] Field of Search .................. 560/183, 184, 186

[56] References Cited

U.S. PATENT DOCUMENTS 2,535,010  12/1950  Croxall et al. .................. 560/183
4,115,105   9/1978  Scannell et al. .................. 562/564

FOREIGN PATENT DOCUMENTS 708513  6/1941  Fed. Rep. of Germany .......... 560/183

OTHER PUBLICATIONS

Litvin, E. F. et al., "Stage mechanism of the hydrogenation of linoleates." Izv. Akad. Nauk. SSSR, Ser. Khim. (1971) 1464–1468. (See Chemical Abstracts 75 (1971) #97,941s).

Mikhant'eva, O. N. et al., "Synthesis of ethylene glycol vinyl heptyl and allyl heptyl ethere." Tr. Voronezh. Gos. Univ. (1969) 73(2)19–20. (See Chemical Abstracts 75 (1971) #152,115e).

Kirk-Othmer Ency. of Chemical Technology, 2nd Ed., vol. 8, pp. 474–475, (1966).

Ibid, 1st Ed., vol. 3, p. 183, (1949).

Sokol'skii, D. V. et al., "Relation between structure and reactivity during the hydrogenation of unsaturated aliphatic nitriles and acids with conjugated bonds. (See Chemical Abstracts 70 (1969), #28,142s.

Houben–Weyl, "Methoden der organischen Chemie", George Thieme, Verlag Band VII, Teil 1, at p. 436.

*Primary Examiner*—Natalie Trousof
*Assistant Examiner*—L. Hendriksen
*Attorney, Agent, or Firm*—Toren, McGeady and Stanger

[57] ABSTRACT

3-Alkoxy-2-alkyl-propionic acid derivatives are prepared by catalytic hydrogenation of the acrylic acid analogs. The latter are obtained by CO treatment of lower alkyl esters of alkanoic acids having 3–6 carbon atoms in the presence of alkali metal methylate and condensation of the resulting 2-formylalkanoic acids or their alkali metal enolates with compounds of the formula X—$(CH_2)_m$—Z wherein X is Cl, Br, or OH, and Z is Cl, Br, I, alkyl- or arylsulfonyl, or OH.

6 Claims, No Drawings

METHOD OF PREPARING A 3-ALKOXY-2-ALKYL-PROPIONIC ACID ESTER DERIVATIVE AND INTERMEDIATE THEREFOR

This invention relates to the preparation of 3-halogenalkoxy-2-alkyl-propionic acid esters and 3-hydroxyalkoxy-2-alkyl-propionic acid esters which are necessary intermediates in the synthesis of 2-[2-(3-acetamino-2,4,6-triiodophenoxy)ethoxy]-methyl-butyric acid, a known orally ingested contrast agent for radiography of the gall bladder [see E. Felder et al., "Il Farmaco" 31 (1976) (ed. prat.) 283, (ed. Sci.) 349].

A known method of making the intermediates (German Pat. No. 2,128,902) employs relatively costly starting materials, has only moderate yields, and relies on halogenalkoxy-methyl chlorides as necessary reagents. The latter are known to be toxic and carcinogenic and are invariably contaminated with bis(chloromethyl) ether whose carcinogenic effects in minute amounts are well known.

They may also be prepared in analogy to a method first described by Lapkin (Chem. Abstr. 65 [1966] 8753c) from chloroalkoxy-methyl chloride by reaction with 2-bromoalkanoic acid esters in the presence of zinc with better yields than in the first-mentioned known method, but without avoiding the use of the dangerous carcinogens.

It is the object of the invention to provide a method of preparing 3-halogenalkoxy and 3-hydroxyalkoxy-2-alkyl-propionic acid esters in a relatively simple manner from inexpensive and hygienically acceptable reactants in good yield.

The desired compounds are 3-alkyloxy-2-alkyl-propionic acid ester derivatives of the formula (I)

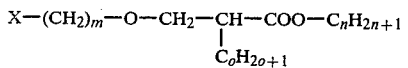

wherein X is chlorine, bromine, or hydroxyl, m is an integer between 2 and 4, and n and o are integers between 1 and 4. It has been found that they are readily prepared from their acrylic acid analogs by catalytic hydrogenation, and that the acrylic acid analogs, which are new compounds, may be prepared in few steps in satisfactory yields.

First an ester of the formual (II)

$$C_oH_{2o+1}-CH_2-COO-C_nH_{2n+1}$$

wherein n and o are as in formula (I), is reacted with carbon monoxide in the presence of an alkali metal alcoholate until a formylation product of the formula (III)

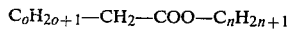

is formed in which Y may be hydrogen or alkali metal.

When the derivative of formula (III) is held under condensation conditions with a compound of the formula (IV)

$$X-(CH_2)_m-Z$$

the desired acrylic acid analog of the formula (V)

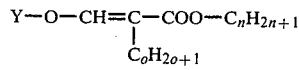

is formed if Y is alkali metal and Z is chlorine, bromine, iodine, alkylsulfonyloxy, or arylsulfonyloxy, the latter two compounds having 1 to 7 carbon atoms. If Y is hydrogen, Z should be hydroxyl, all other symbols being as explained above.

2-Formyl-alkanoic acid esters of formula (III) were prepared heretofore from esters of formula (II) by reaction with formic acid esters in the presence of basic condensation agents, such as sodium or sodium alcoholates (J. Chem. Soc. 121 [1922] 1782; German Pat. No. 708,513). It has been found that the expensive formic acid esters can be avoided by the use of carbon monoxide at moderately elevated pressure in the presence of alkali metal alcoholates. While other alkali metal moieties and alcohol moieties having up to five carbon atoms are operative in the method, the other alkali metal alcoholates do not offer any advantages over the inexpensive, readily available sodium methylate.

The further reaction of the formyl-alkanoic acid esters with alcohols to the corresponding enol-ethers is not basically novel. Gannon et al [Organic Syntheses 40 (1960) 41] have described the conversion of dihydroresorcinol to 3-ethyloxy-2-cyclohexenone by means of ethanol in the presence of toluenesulfonic acid. The reaction of alkali metal enolates with alkyl halides is described in "Methoden der Organischen Chemie" by Houben-Weyl (6/3.109-110 [1965]), but enol ethers are considered very labile compounds which are hydrolyzed by water (Houben-Weyl 7/1.46 [1954]). Their application to reactions of the type employed by this invention, however, is not suggested by any earlier work of others.

We have found that the hydrogenation of an enol ether was performed prior to our invention, though in a very different context. Feely et al. [Organic Syntheses 38 (1958) 22] subjected ethoxymethylene-malonic acid diethylester to catalytic hydrogenation and heated the intermediate so produced, probably 2-ethoxymethyl-malonic acid diethyl ester to produce methylene-malonic acid diethyl ester. The analogy between this earlier work and our method, however, is remote.

It was rather surprising that halogen in the 3-alkoxy moiety of our acrylic acid analog was not replaced by hydrogen even during catalytic hydrogenation at high pressure.

The following Examples are further illustrative of the method of the invention.

EXAMPLE 1

3-(2-Chloroethoxy)-2-ethyl-propionic acid methyl ester 130 g 85.2% Sodium methylate solution (2 moles) was stirred in a pressure vessel with 1200 ml methyl butyrate (10.6 moles). The vessel was charged with carbon monoxide until a gage pressure of 10 atmospheres was reached. The vessel then was held at 60° C. for six hours, and the carbon monoxide consumed was replaced in four separate batches. The reaction mixture was cooled to ambient atmosphere and mixed with 500 g ice and 150 ml glacial acetic acid. An organic phase separated from a heavier aqueous phase, was withdrawn, dried, and fractionated in a vacuum.

In two successive runs under identical conditions, 229 g and 234.3 g 2-formyl-butyric acid methyl ester boiling at 50 torr and 72° C. and 70° C. respectively was obtained for a yield of 88–90%, based on the sodium methylate employed. The unreacted methyl butyrate was recovered during fractionation.

35 g 2-Formyl-butyric acid methyl ester (0.27 mole) was dissolved in 250 ml benzene, and the solution was mixed with 26 g 2-chloroethanol (0.324 mole) and 700 mg sodium bisulfate. The mixture was refluxed for 18 hours, and the water formed during the reaction was withdrawn continuously. After removal of the solvent by distillation, the residue was fractionated in a vacuum and 42.8 g (44.2 g) 3-(2-chloroethoxy)-2-ethylacrylic acid methyl ester boiling at 99°–101° C./3 torr was obtained (82.4%–85% yield). $n_D^{23} = 1.4770$.

A small amount of a fraction boiling at 102°–130°/3 torr consisted largely of 3,3-bis-(2-chloroethoxy)-2-ethylpropionic acid methyl ester which could be converted to the desired 3-(2-chloroethoxy)-2-ethyl-acrylic acid ester by refluxing in benzene in the presence of NaHSO$_4$.

37 g of 3-(2-Chloroethoxy)-2-ethylacrylic acid methyl ester (0.192 mole) was dispersed in 350 ml ethanol together with 6 g Raney nickel catalyst. The mixture was hydrogenated in a pressure vessel at 55°–60° C. at a hydrogen gage pressure of 30–60 atmospheres. When no further hydrogen was absorbed, the contents of the vessel were filtered to remove the catalyst, the solvent was distilled off, and the residue was fractionated in a vacuum. 3-(2-Chloroethoxy)-2-ethylpropionic acid methyl ester was obtained in an amount of 30.7 g (33.7 g) as a fraction boiling at 110° C. and 14 torr (82%–90% yield). $n_D^{20} = 1.4399$, $d_4^{20} = 1.083$.

Selective hydrogenation at the double bond was achieved also at atmospheric pressure in the presence of a palladium catalyst on a carbon carrier (5% Pd).

EXAMPLE 2

3-(2-Chloroethoxy)-2-ethylpropionic acid ethyl ester 1200 g Ethyl butyrate was reacted with 130 g 85% sodium methylate substantially as in Example 1 to produce 245 g 2-formylbutyric acid ethyl ester (85% yield) boiling at 60°–64° C./14 torr. $n_{20}^D = 1.4300$.

28.8 g 2-Formyl-butyric acid ethyl ester was refluxed in 250 ml benzene with 54 g 2-chloroethanol in the presence of 250 mg sodium bisulfate, and the water of reaction formed thereby was withdrawn continuously. Conditions analogous to those in Example 1 were maintained to produce 34.5 g 3-(2-chloroethoxy)-2-ethylacrylic acid ethyl ester (84% yield) boiling at 104°–107° C./2 torr. $n_D^{23} = 1.4719$. The compound was hydrogenated as in Example 1, and 3-(2-chloroethoxy)-2-ethylpropionic acid ethyl ester was obtained in a yield of 81.5%. It boiled at 120°–122° C./14 torr, $n_D^{27} = 1.4352$.

EXAMPLE 3

3-(2-Bromoethoxy)-2-ethylpropionic acid methyl ester 70 g 2-Formyl-butyric acid methyl ester (0.54 mole), 135 g 2-bromoethanol (1.08 mole) and 1.4 g sodium bisulfate were refluxed with stirring, and the water formed during the reaction was continuously withdrawn by means of a Dean-Stark separator until 12.5 g aqueous liquid was removed over a period of 15 hours. The solvent was then evaporated from the reaction mixture, and the residue was fractionated in a vacuum. A fraction boiling at 86°–88° C./0.1 torr weighed 109 g (85% yield). $n_D^{20} = 1.4971$. It was identified as 3-(2-bromoethoxy)-2-ethyl-acrylic acid methyl ester by its bromine content of 33.47% (33.70% calculated for $C_8H_{13}BrO_3$).

47.4 g 3-(2-Bromoethoxy)-2-ethyl-acrylic acid methyl ester was hydrogenated in 300 ml methanol in the presence of 8 g 5% moist palladium-carbon catalyst at ambient temperature and pressure. After 75% of the expected amount of hydrogen had been consumed, the hydrogenation mixture was heated at 50° C. while the remaining 25% of the hydrogen was absorbed. When a sample of the filtered reaction mixture was titrated with silver nitrate, only approximately 1.1% of the bromine originally present was found in the form of bromine ions.

The solvent was evaporated from the filtered hydrogenation mixture, and the residue was distilled in a vacuum. 38.7 g 3-(2-bromoethoxy)-2-ethyl-propionic acid methyl ester boiling at 123°–125° C./14 torr was recovered (81% yield). $n_D^{20} = 1.4589$. It was identified by its bromine content of 33.58% (33.41% calculated for $C_8H_{15}BrO_3$).

EXAMPLE 4

3-(2-Chloroethoxy)-2-ethyl-propionic acid methyl ester 40 kg p-Toluenesulfonyl chloride was added to 60.4 kg pyridine at −10° C. The mixture was further cooled to −5° C., and 14.5 kg ethylene chlorohydrin was added continuously with agitation over a period of four hours. The reaction mixture then was stirred into a mixture of 125 kg water, 125 kg ice, and 60 kg methylene chloride. Hydrochloric acid 1:1 then was added at temperature not exceeding 10° C. until the pH reached a value of 3.

The methylene chloride phase was recovered, washed with water and then with sodium bicarbonate solution, dried, and stripped of solvent by evaporation. The residue consisted of 44.8 kg 2-(p-toluenesulfonyloxy)-ethyl chloride boiling at 110°–115° C./0.01 torr.

1021 g Methyl butyrate (10 moles), 225 g 96% sodium methylate (4 mole), and 40 ml methanol were mixed in a pressure vessel, and carbon monoxide was introduced until a gage pressure of 60 atmospheres was reached. The contents of the vessel were heated at 60°–65° C., and the carbon monoxide consumed by the ensuing reaction was replaced repeatedly to maintain a pressure of 40 atmospheres. The reaction was completed after about two hours, and the contents of the pressure vessel were then evaporated to dryness in a vacuum. 529 g Unreacted methyl butyrate was recovered from the distillate. The residue weighing 620 g consisted largely of the sodium enolate of 2-formyl-butyric acid methyl ester.

It was dispersed in 1.8 liters dimethylacetamide, the resulting slurry was mixed with 845 g 2-(p-toluenesulfonyloxy)-ethyl chloride, and the mixture was agitated at 30° C. for 15–20 hours. It was then stirred into ice water and adjusted to pH 7 with acetic acid. The 3-(2-chloroethoxy)-2-ethyl-acrylic acid methyl ester was extracted with methylene chloride, and the extract was washed with water, dried, and partly evaporated. The residue was distilled in a vacuum to produce 513 g 3-(2-chloroethoxy)-2-ethyl-acrylic acid methyl ester boiling at 72°–75° C./0.1 torr.

The yield was 74% based on the 2-p-toluenesulfonyloxyethyl chloride, and 67% based on the sodium methylate.

346.8 g 3-(2-Chloroethoxy)-2-ethyl-acrylic acid methyl ester was hydrogenated in 1200 ml methanol in the presence of 27 g 5% palladium-carbon catalyst at atmospheric pressure. The amount of hydrogen required to saturate the double bond was absorbed within approximately 90–120 minutes, whereupon the catalyst was filtered off, and the filtrate was partly evaporated. The residue was distilled in a vacuum to produce 305 g 3-(2-chloroethoxy)-2-ethyl-propionic acid methyl ester (87% yield) boiling at 110°–112° C./14 torr.

EXAMPLE 5

3-(2-Hydroxyethoxy)-2-ethyl-propionic acid methyl ester 62 g sodium enolate of 2-formyl-butyric acid methyl ester was prepared as in Example 4 and slurried in 180 ml dimethylacetamide. 32 g 2-chloroethanol was added, and the mixture was stirred on a boiling water bath for 15–20 hours. It was then worked up in the manner described in more detail in Example 4, and 28.75 g 3-(2-hydroxyethoxy)-2-ethyl-acrylic acid methyl ester boiling at 110°–116° C./0.1 torr was obtained (41% yield). It was identified by its carbon content of 53.33% (55.10% calculated for $C_8H_{14}O_4$).

28 g 3-(2-hydroxyethoxy)-2-ethyl-acrylic acid methyl ester was hydrogenated in 100 ml methanol in the presence of 2 g 5% palladium-carbon catalyst at atmospheric pressure. 24 g 3-(2-hydroxyethoxy)-2-ethyl-propionic acid methyl ester boiling at 104°–107° C./0.1 torr (84% yield) was recovered from the filtered hydrogenation mixture after evaporation of the solvent and vacuum distillation and identified by its carbon content of 54.35% (54.54% calculated for $C_8H_{16}O_4$).

EXAMPLE 6

3-(4-Chlorobutoxy)-2-butyl-propionic acid methyl ester 162.5 g Methyl caproate (1.25 mole), 28 g 96% sodium methylate (0.5 mole), and 10 ml methanol were reacted with carbon monoxide in the manner described in Example 4, and approximately 100 g crude sodium enolate of 2-formylcaproic acid methyl ester was obtained as an evaporation residue. It was suspended in 180 ml dimethylacetamide and mixed with 103 g 4-chlorobutyl bromide. The mixture was stirred about 4–6 hours at 65°–70° C., and worked up in a manner analogous to the procedure of Example 5. 74.5 g 3-(4-chlorobutoxy)-2-butyl-acrylic acid methyl ester boiling at 155° C./2 torr was obtained for a 60% yield based on the sodium methylate employed.

When 62.2 g (0.25 mole) 3-(4-chlorobutoxy)-2-butyl-acrylic acid methyl ester was catalytically hydrogenated as in Example 4, 47 g 3-(4-chlorobutoxy)-2-butyl-propionic acid methyl ester of boiling point 142° C./2 torr was recovered (75% yield). It was identified by its chlorine content of 14.30% (14.14% calculated for $C_{12}H_{23}ClO_3$).

EXAMPLE 7

3-(2-Chloroethoxy)-2-methyl-propionic acid propyl ester 145 g Propyl propionate (1.25 moles), 28 g 96% sodium methylate (0.5 mole) and 10 ml methanol were reacted with carbon monoxide as in Example 4, and the formylation mixture was worked up to produce 92 g evaporation residue which was reacted with 141 g 2-(p-toluenesulfonyloxy)-ethyl chloride at 30° C. in the manner of Example 4. Upon an analogous work-up, 67.13 g 3-(2-chloroethoxy)-2-methyl-propionic acid propyl ester boiling at 97°–99° C./1 torr (65% yield) was obtained. It was hydrogenated in methanol at atmospheric pressure, as in Example 4, and 3-(2-chloroethoxy)-2-methyl-propionic acid propyl ester boiling at 102°–105° C./5 torr was recovered in a yield of 89%. It contained 16.8% chlorine (17.0% calculated for $C_9H_{17}O_3Cl$).

As is evident from the Examples, the mole ratio of sodium methylate to the ester during the formylation reaction determines whether the free aldehyde or the sodium enolate is obtained directly in the first stage of this method, and either one or the other will preferably be chosen depending on the nature of the substituent Z in the condensation partner for the formylation product in the second stage of the invention.

It should be understood, of course, that the foregoing disclosure relates only to preferred embodiments, and that it is intended to cover all changes and modifications of the examples of the invention herein chosen for the purpose of the disclosure which do not constitute departures from the spirit and scope of the invention set forth in the appended claims.

What is claimed is:

1. A method of preparing a 3-alkyloxy-2-alkyl-propionic acid ester derivative of the formula (I)

$$X-(CH_2)_m-O-CH_2-\underset{\underset{C_oH_{2o+1}}{|}}{CH}-COO-C_nH_{2n+1}$$

which comprises:
(a) reacting an ester of the formula (II)

$$C_oH_{2o+1}-CH_2-COO-C_nH_{2n+1}$$

with carbon monoxide in the presence of an alkali metal alcoholate until a formylation product of the formula (III)

$$Y-O-CH=\underset{\underset{C_oH_{2o+1}}{|}}{C}-COO-C_nH_{2n+1}$$

is formed;
(b) holding said product of formula (III) under condensation conditions with a compound of the formula (IV)

$$X-(CH_2)_m-Z$$

until the acrylic acid analog of said derivative of formula (I) is formed as the compound of the formula (V)

$$X-(CH_2)_m-O-CH=\underset{\underset{C_oH_{2o+1}}{|}}{C}-COO-C_nH_{2n+1}$$

and
(c) hydrogenating said acrylic acid analog to said derivative of formula (I);
(d) in said formulas:
X being chlorine, bromine, or hydroxyl,
Y being hydrogen or alkali metal,
Z being chlorine, bromine, iodine, alkylsulfonyloxy, or arylsulfonyloxy, alkyl and aryl in said alkylsulfonyloxy or arylsulfonyloxy having 1 to 7 carbon atoms, when Y is alkali metal; Z being hydroxyl when Y is hydrogen
m being an integer between 2 and 4, n and o being integers between 1 and 4.

2. A method as set forth in claim 1, wherein Y is alkali metal, X is halogen, Z is alkylsulfonyloxy or arylsulfonyloxy, and said acrylic acid analog is hydrogenated in the presence of a hydrogenation catalyst.

3. A method as set forth in claim 2, wherein Y is sodium, X is chlorine, m and o are 2, and n is 1.

4. A method as set forth in claim 3, wherein Z is p-toluenesulfonyloxy.

5. A 3-alkyloxy-2-alkyl-acrylic acid ester derivative of the formula (V)

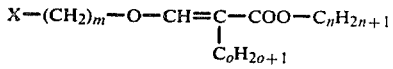

wherein X is chlorine, bromine, or hydroxyl; m is an integer between 2 and 4, and n and o are integers between 1 and 4.

6. A 3-alkyloxy-2-alkyl-acrylic acid ester as set forth in claim 5 wherein X is chlorine, m and o are 2, and n is 1.

* * * * *